United States Patent
Johnson et al.

(10) Patent No.: US 10,105,202 B2
(45) Date of Patent: Oct. 23, 2018

(54) TOOTHBRUSH WITH AUTOMATIC DETECTION OF BRUSHING ANGLE

(71) Applicant: KONINKLIJKE PHILIPS N.V., Eindhoven (NL)

(72) Inventors: Mark Thomas Johnson, Arendonk (BE); Johannes Hendrikus Maria Spruit, Waalre (NL); Okke Ouweltjes, Veldhoven (NL); Edgar Martinus Van Gool, Veghel (NL); Menno Willem Jose Prins, Rosmalen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2 days.

(21) Appl. No.: 15/517,202

(22) PCT Filed: Oct. 5, 2015

(86) PCT No.: PCT/IB2015/057613
§ 371 (c)(1),
(2) Date: Apr. 6, 2017

(87) PCT Pub. No.: WO2016/055925
PCT Pub. Date: Apr. 14, 2016

(65) Prior Publication Data
US 2017/0312062 A1 Nov. 2, 2017

Related U.S. Application Data

(60) Provisional application No. 62/060,824, filed on Oct. 7, 2014.

(51) Int. Cl.
*B08B 7/00* (2006.01)
*A61C 17/22* (2006.01)
(Continued)

(52) U.S. Cl.
CPC .............. *A61C 17/221* (2013.01); *A46B 9/04* (2013.01); *A46B 15/004* (2013.01); *A46B 15/0044* (2013.01); *A46B 15/0046* (2013.01)

(58) Field of Classification Search
CPC ..... A46B 9/04; A46B 15/004; A46B 15/0044; A46B 15/0046; A61C 17/221
See application file for complete search history.

(56) References Cited

U.S. PATENT DOCUMENTS 5,493,747 A 2/1996 Inakagata et al.
6,425,295 B1 * 7/2002 Meginniss ......... A46B 15/0002
73/862.046

(Continued)

FOREIGN PATENT DOCUMENTS

DE 19506129 A1 8/1996
EP 1244373 B1 7/2006
(Continued)

OTHER PUBLICATIONS

Baszynski et al: "3D Posture Measurements in Dental Applications"; VIMS2002 International Symposium on Virtual and Intelligent Measurement Systems, May 2002, 5 Page Document.

*Primary Examiner* — Sharidan Carrillo

(57) ABSTRACT

A toothbrush (10) includes a brushhead (18), a first force sensor (30A) for measuring a first force exerted by the brushhead at a first angle relative to a tooth and a second force sensor (30B) for measuring a second force exerted by the brushhead at a second angle relative to the tooth, the second angle being different than the first angle, and a processing unit (26). The processing unit is structured to: (i) receive first information indicative of the first force as measured by the first force sensor, (ii) receive second information indicative of the second force as measured by the second force sensor, and (iii) determine information
(Continued)

regarding a current brushing angle of the brushhead based on the first information and the second information.

2 Claims, 3 Drawing Sheets

(51) Int. Cl.
    *A46B 15/00*         (2006.01)
    *A46B 9/04*          (2006.01)

(56) References Cited

U.S. PATENT DOCUMENTS

| | | |
|---|---|---|
| 6,536,068 B1 | 3/2003 | Yang et al. |
| 2011/0010876 A1 | 1/2011 | Iwahori et al. |
| 2013/0000670 A1 | 1/2013 | Binner et al. |
| 2015/0202030 A1* | 7/2015 | Miller ................ A46B 15/0012 15/22.1 |
| 2016/0015492 A1* | 1/2016 | Skaanland ......... A46B 15/0012 15/22.2 |
| 2017/0303673 A1* | 10/2017 | Van Gool .......... A46B 15/0006 |
| 2017/0312062 A1* | 11/2017 | Johnson ............... A61C 17/221 |

FOREIGN PATENT DOCUMENTS

| | | | |
|---|---|---|---|
| JP | S62109081 A | 5/1987 |
| JP | 2013009958 A | 1/2013 |
| WO | 0215742 A2 | 2/2002 |
| WO | 2011073010 A1 | 6/2011 |
| WO | 2014097242 A1 | 6/2014 |

\* cited by examiner

TOOTHBRUSH WITH AUTOMATIC DETECTION OF BRUSHING ANGLE

CROSS-REFERENCE TO PRIOR APPLICATIONS

This application is the U.S. National phase application under 35 U.S.C § 371 of international Application No. PCT/IB2015/057613, filed on Oct. 5, 2015, which claims the benefit of U.S. Provisional Patent Application No. 62/060,824, filed on Oct. 7, 2014. The applications are incorporated by reference herein.

BACKGROUND OF THE INVENTION

1. Field of the Invention

The present invention pertains to toothbrushes, and, in particular, to a toothbrush, such as a power toothbrush, structured to detect brushing angle and provide feedback to the user based on brushing force detected at a plurality of angles.

2. Description of the Related Art

In general, power toothbrushes for cleaning teeth, including removal of plaque, are well known. Typically, power toothbrushes rely on a set of bristles which are attached to a bristle mounting plate, which in turn is moved by a driver mechanism to scrub the surfaces of teeth. Such toothbrushes, which rely on scrubbing action of the bristles for actual cleaning, typically require some amount of force to be exerted by the user against the teeth to accommodate differences in the various shapes and spacing of the teeth and to effectively clean the teeth.

Correct positioning of the bristles of a toothbrush relative to the teeth is essential for efficient plaque removal. To best remove plaque from the teeth, it is often advantageous to brush with the bristles positioned at an angle fairly perpendicular to the tooth. Trials have revealed that users regularly brush their teeth at angle far from the perpendicular. Angles of up to 70 degrees from the perpendicular are common, especially when brushing the inside of the teeth. At such extreme angles, many of the bristles are no longer in contact with the teeth (or are at an inefficient angle) and brushing is extremely inefficient.

SUMMARY OF THE INVENTION

In one embodiment, a toothbrush is provided that includes a brushhead, a first force sensor for measuring a first force exerted by the brushhead at a first angle relative to a tooth and a second force sensor for measuring a second force exerted by the brushhead at a second angle relative to the tooth, the second angle being different than the first angle, and a processing unit. The processing unit is structured to: (i) receive first information indicative of the first force as measured by the first force sensor, (ii) receive second information indicative of the second force as measured by the second force sensor, and (iii) determine information regarding a current brushing angle of the brushhead based on the first information and the second information.

In another embodiment, a method of operating a toothbrush having a brushhead is provided. The method includes generating first information indicative of a first force exerted by the brushhead at a first angle relative to a tooth and second information indicative of a second force exerted by the brushhead at a second angle relative to the tooth, the second angle being different than the first angle, determining information regarding a current brushing angle of the brushhead based on the first information and the second information, and providing user perceptible feedback based on the determined information regarding the current brushing angle.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
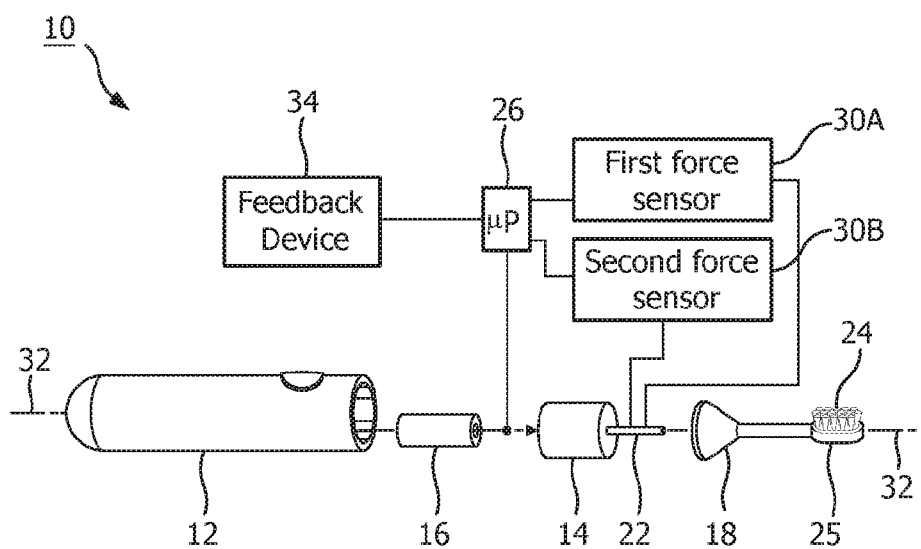
FIG. 1 is an exploded schematic view of a toothbrush according to an exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, "substantially perpendicular" shall mean at an angle of 90 degrees ±5 degrees.

As used herein, "substantially parallel" shall mean at an angle of 0 degrees ±5 degrees.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
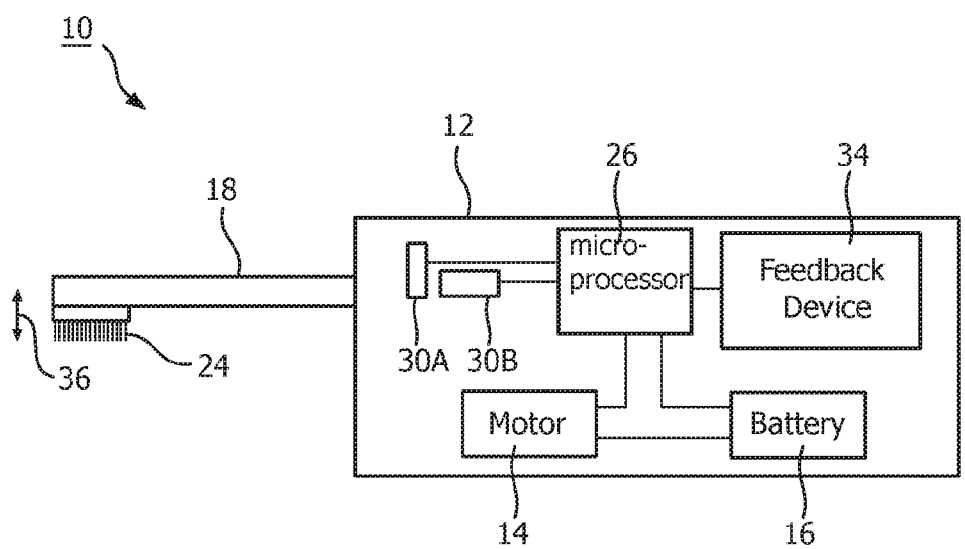
FIG. 2 is a schematic diagram of the toothbrush of FIG. 1.

FIG. 1 is an exploded schematic view of and FIG. 2 is a schematic diagram of a power toothbrush 10 according to an exemplary embodiment of the present invention. As described in detail herein, toothbrush 10 is structured to detect brushing force at a plurality of angles which, unlike prior art toothbrushes that may have a single force sensor, allows for the brushhead angle, and thus the brushing angle, to be derived. Toothbrush 10 includes a handle portion 12 and a DC motor 14 which is powered by a battery 16. Motor 14 provides the driving action for a brushhead 18, which in turn is removably mounted on a motor driveshaft 22. It should be understood, however, that various alternative driving action arrangements may be used in a power toothbrush which incorporates the concept disclosed herein. The illustration of a DC motor in the exemplary embodiment is only one of several possible motor systems.

Brushhead 18 includes a set of bristles 24 mounted on a bristle back member 25 which together define the bristle portion of brushhead 18. Bristles 24 accomplish cleaning through an oscillatory action provided to brushhead 18 by motor 14. The operation of motor 14 is controlled by a processing unit 26, which is a common component of power toothbrushes. Processing unit 26 may be, for example and without limitation, a microprocessor, a microcontroller, or any other suitable processing device and may include a suitable memory for storing routines executed by processing unit 26.

As seen in FIGS. 1 and 2, in the exemplary embodiment, handle portion 12 includes a first force sensor 30A for measuring the brushing force exerted by brushhead 18 against the teeth during use of toothbrush 10 at a first angle relative to a longitudinal axis 32 of toothbrush 10 and a longitudinal axis 36 of bristles 24 (as indicated by arrow in FIG. 2), and a second force sensor 30B for measuring the brushing force exerted by brushhead 18 against the teeth during use of toothbrush 10 at a second angle relative to the longitudinal axis 32 of toothbrush 10 and longitudinal axis 36 of bristles 24 (different than the first axis). In the exemplary embodiment, first force sensor 30A and second source sensor 30B are located adjacent to motor 14 and are structured to measure the force on driveshaft 22. Thus, first force sensor 30A and second source sensor 30B are structured and positioned to measure brushing forces at two different angles. For example, first force sensor 30A may be structured and positioned to measure brushing force at an angle that is substantially perpendicular to the longitudinal axis 32 of toothbrush 10 and substantially parallel to the longitudinal axis 36 of bristles 24 and second force sensor 30B may be structured and positioned to measure brushing force at an angle that is substantially parallel to the longitudinal axis 32 and substantially perpendicular to the longitudinal axis 36 of bristles 24. It will be appreciated, however, that this configuration is meant to be exemplary only, and that alternative angles for each force sensor 30A and 30B are also possible within the scope of the concept disclosed herein. A number of exemplary alternative configurations for force sensors 30A and 30B are described in detail elsewhere herein. In addition, as seen in FIGS. 1 and 2, first force sensor 30A and second force sensor 30B are each operatively coupled to processing unit 26 and provide a signal to processing unit 26 indicative of the force measured thereby. In an alternative embodiment, force sensors 30A and 30B may be located in brushhead 18. However, as will be appreciated, the former configuration wherein force sensors 30A and 30B are located within handle portion 12 will help to keep the cost of brushhead 18 down and will avoid interconnection issues across the pluggable interface between brushhead 18 and handle portion 12.

First force sensor 30A and second force sensor 30B may be any of a number of known or hereafter developed suitable sensing devices for sensing the force exerted by brushhead 18. For example, and without limitation, first force sensor 30A and second force sensor 30B may each be a strain gauge structured to directly measure the brushing force or a sensor, such as a magnetic (Hall) sensor, which indirectly measures the brushing force by measuring the displacement of brushhead 18 and/or motor driveshaft 22.

The measured force values generated by first force sensor 30A and second force sensor 30B are provided to processing unit 26. Furthermore, as seen in FIGS. 1 and 2, handle portion 12 also includes a feedback device 34 that is coupled to processing unit 26. As described in greater detail herein, during use of toothbrush 10, feedback device 34 is structured to provide user perceptible feedback regarding the brushing angle with respect to the tooth surfaces (i.e., the brushing angle at which bristles 24 are positioned) that the user is employing at any particular time. The user perceptible feedback generated by feedback device 34 is designed to encourage the user to brush at a favorable brushing angle. A number of manners in which the brushing angle and or feedback may be determined and/or provided are described in detail herein. Feedback device 34 may be an audible feedback device, such as a speaker, that is structured to generate an audible feedback signal under the control of processing unit 26. Alternatively, feedback device 34 may be a visual feedback device, such as one or more LEDs, that is/are structured to generate a visual feedback signal under the control of processing unit 26. In still another alternative embodiment, the feedback may be implemented by processing unit 26 modifying the motor drive mode of motor 14 to give a different sensation in the user's mouth, such as a lowered amplitude, a pulsing of the motor 14, or some other alternation of the motor vibration. Such a feedback mechanism may be more easily perceived by the user.

Figure 5:
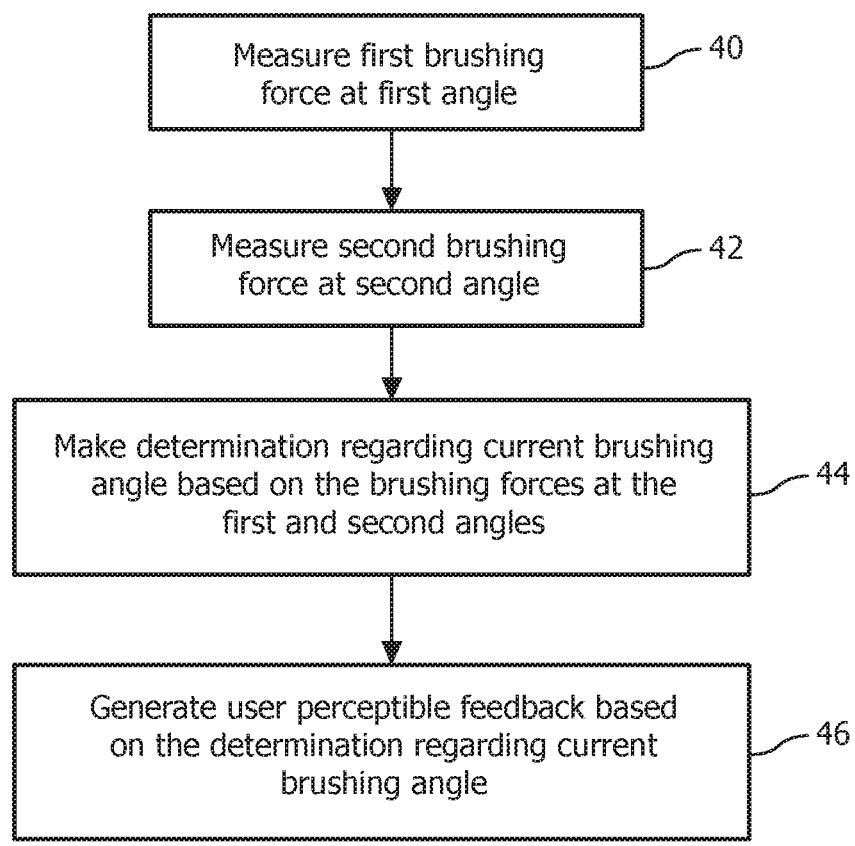
FIG. 5 is a flowchart illustrating operation of the toothbrush of FIGS. 1 and 2 according to one exemplary embodiment.

FIG. 5 is a flowchart illustrating a method of operation of toothbrush 10 according to an exemplary embodiment of the disclosed concept wherein a determination of current brushing angle is made/derived based upon brushing forces that are measured at two or more different angles and wherein, in response thereto, feedback is provided to the user of toothbrush 10 in order to encourage a preferred brushing angle. The method begins at step 40, wherein a first brushing force is measured at a first angle by first force sensor 30A (referred to herein as $F_1$). Then, at step 42, a second brushing force is measured at a second angle different than the first angle by second force sensor 30B (referred to herein as $F_2$). The first and second brushing forces measured at step 40 and 42 are provided to processing unit 26. Next, at step 44, processing unit 26 makes a determination regarding the current brushing angle based on the first and second brushing forces that were measured at step 40 and 42. In the exemplary embodiment, the determination made at step 44 is a determination as to the degree to which the brushing angle is something other than substantially perpendicular to the surface of the teeth (i.e., the degree of rotation of brushhead 18 and in particular bristles 24 and bristle back member 25 about longitudinal axis 32 during brushing). For example, and without limitation, step 44 may involve determining whether, based on the first and second brushing forces, the brushing angle is within an ideal range, a non-ideal yet still acceptable range, or an unacceptable range. As another, simpler example, step 44 may involve determining whether the brushing angle is above or below a suitable predetermined threshold for acceptable angle. Still other examples are within the scope of the disclosed concept. Finally, at step 46, processing unit 26 causes a user perceptible feedback to be generated through feedback device 34 based on the determination made in step 44. For example, and without limitation, the user perceptible feedback may be causing a particularly colored LED or LEDs forming part of feedback device 34 to be lit and/or may be causing an audible signal of a particular nature to be generated feedback device 34 (for instance, a buzzing sound may be generated in the case where the brushing angle is determined to be in an unacceptable range and/or below a suitable predetermined threshold).

A number of non-limiting, exemplary implementations of the method of FIG. 5 will now be described in detail. It will be understood, however, that the implementations described below are meant to be exemplary only and thus are not to be considered limiting.

In a first exemplary implementation, first force sensor 30A is structured to measure a force $F_1$ at a first angle that is substantially perpendicular to the longitudinal axis 32 and substantially parallel to the longitudinal axis 36 of bristles 24 and second force sensor 30B is structured to measure a force $F_2$ at a second angle that is substantially parallel to longitudinal axis 32 and substantially perpendicular to the longitudinal axis 36 of bristles 24. In this exemplary implementation, the determination regarding current brushing angle can be made using the case analysis shown in TABLE 1 below, wherein $F_T$ is a typical brushing force of the user of, for example and without limitation, 1-3N

TABLE 1

| Use Case | $F_1$ value | $F_2$ value | Determination regarding current brushing angle |
| --- | --- | --- | --- |
| Case 1 | $F_T$ | 0 | Brushing is perpendicular to the tooth surface - Ideal brushing |
| Case 2 | ~$F_T$ | >0 | Brushing is not perpendicular to the tooth surface - Non ideal but still acceptable brushing |
| Case 3 | <$F_T$ | >>0 | Brushing is not perpendicular to the tooth surface - Less than acceptable (i.e., inefficient) brushing |
| Case 4 | <<$F_T$ | F2 >>> 0 | Brushing is at a very high angle to the tooth surface - Very inefficient brushing |

Based on the case analysis described above, if processing unit 26 determines that the current brushing of the user falls within Case 3 or Case 4, and thus that the brushing angle is unfavorable and/or unacceptable, then processing unit 26 will, in the exemplary embodiment, cause feedback device 34 to provide a corrective signal to the user, such as an alarm sound or a light of a particular color, in order to encourage the user to brush at a better angle.

In the case analysis described above, the proposed figure of merit is the ratio of the measured forces $F_1/(F_1+F_2)$. Thus, the case analysis described above may, in one particular embodiment, be implemented based on the information/formulas provided in TABLE 2 below.

TABLE 2

| $F_1/(F_1 + F_2)$ Ratio | Determination regarding current brushing angle |
| --- | --- |
| $F_1/(F_1 + F_2)$ > Threshold$_1$ | ideal brushing (green LED lit) |
| Threshold$_2 \leq F_1/(F_1 + F_2) \leq$ Threshold$_1$ | non-ideal brushing (orange LED lit) |
| $F_1/(F_1 + F_2)$ < Threshold$_2$ | bad brushing (red LED lit) |

In one particular, non-limiting embodiment, Threshold$_1$=0.8 and Threshold$_2$=0.5. In a simplified example, the case analysis described above may be implemented based upon and using a single feedback formula as follows: if $F_1/(F_1+F_2)$<Threshold$_3$: bad brushing (red LED lit and/or buzzer sound activated); otherwise brushing angle acceptable. In one particular, non-limiting embodiment, Threshold$_3$=0.65.

Figure 3:
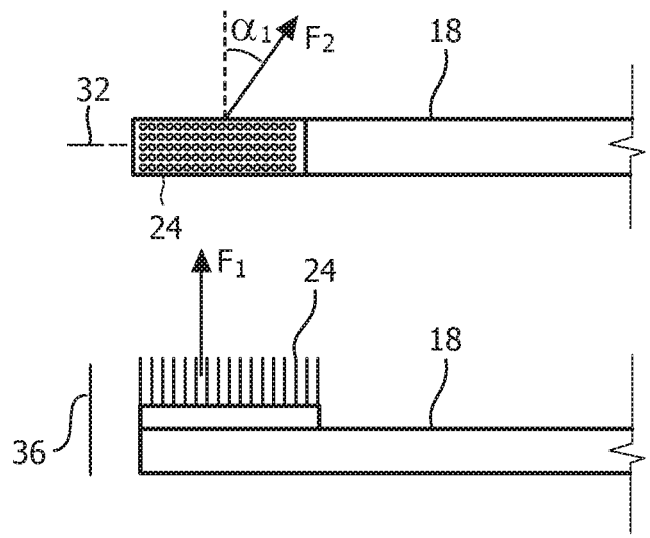
FIGS. 3 and 4 are schematic diagrams illustrating two alternative particular implementations of the toothbrush head of FIGS. 1 and 2.

In a second exemplary implementation of toothbrush 10, shown schematically in FIG. 3, first force sensor 30A is structured to measure a force $F_1$ at a first angle that is substantially perpendicular to the longitudinal axis 32 and substantially parallel to the longitudinal axis 36 of bristles 24 and second force sensor 30B is structured to measure a force $F_2$ at a second angle that is substantially perpendicular to the longitudinal axis 36 of bristles 24 and that is at an angle $\alpha_1$ that is not substantially perpendicular to longitudinal axis 32 (as demonstrated in FIG. 3). In this second alternative exemplary implementation, a reduction factor of about the cosine of $\alpha_1$ is applied and the case analysis described herein may be implemented based on the information/formulas provided in TABLE 3 below.

TABLE 3

| $F_1/(F_1 + F_2/\cos \alpha_1)$ Ratio | Determination regarding current brushing angle |
| --- | --- |
| $F_1/(F_1 + F_2/\cos \alpha_1)$ > Threshold$_1$ | ideal brushing (green LED lit) |
| Threshold$_2 \leq F_1/(F_1 + F_2/\cos \alpha_1) \leq$ Threshold$_1$ | non-ideal brushing (orange LED lit) |
| $F_1/(F_1 + F_2/\cos \alpha_1)$ < Threshold$_2$ | bad brushing (red LED lit) |

In a simplified example, the case analysis in this alternative may be implemented based upon and using the single feedback formula as follows: if $F_1/(F_1+F_2/\cos \alpha_1)$<Threshold$_3$: bad brushing (red LED lit and/or buzzer sound activated); otherwise brushing angle acceptable.

Figure 4:
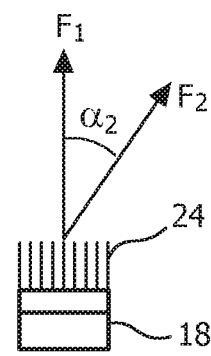

In a third exemplary implementation of toothbrush 10, shown schematically in FIG. 4, first force sensor 30A is structured to measure a force $F_1$ at a first angle that is substantially perpendicular to the longitudinal axis 32 and substantially parallel to the longitudinal 36 axis of bristles 24 and second force sensor 30B is structured to measure a force $F_2$ at a second angle that is at an angle $\alpha_2$ that is not substantially perpendicular to the longitudinal axis 36 of bristles 24 and that is substantially perpendicular to longitudinal axis 32 (as demonstrated in FIG. 4). In this third alternative exemplary implementation, a reduction factor of about the sine of $\alpha_2$ is applied and the case analysis described herein may be implemented based on the information/formulas provided in TABLE 4 below.

TABLE 4

| $F_1/(F_1 + F_2/\sin\alpha_1)$ Ratio | Determination regarding current brushing angle |
| --- | --- |
| $F_1/(F_1 + F_2/\sin\alpha_2)$ > Threshold$_1$ | ideal brushing (green LED lit) |
| Threshold$_2 \leq F_1/(F_1 + F_2/\sin\alpha_2) \leq$ Threshold$_1$ | non-ideal brushing (orange LED lit) |
| $F_1/(F_1 + F_2/\sin\alpha_2)$ < Threshold$_2$ | bad brushing (red LED lit) |

In a simplified example, the case analysis in this alternative may be implemented based upon and using the single feedback formula as follows: $F_1/(F_1+F_2/\sin\alpha_2)$<Threshold$_3$: bad brushing (red LED lit and/or buzzer sound activated); otherwise brushing angle acceptable.

In a fourth exemplary implementation, first force sensor 30A and second force sensor 30B are both positioned at angles that are not substantially perpendicular to longitudinal axis 36 of bristles 24. In this case, it may be advantageous if both first and second force sensors 30A and 30B have the same angle relative to longitudinal axis 36 of bristles 24. The force measured by each of the first and second force sensors 30A and 30B will be substantially equal (i.e., the normalized signal $(F_1-F_2)/(F_{1+}F_2){\sim}0$) if the user is brushing substantially perpendicular to the tooth (ideal case), whilst the brushing angle will increase (i.e. become less ideal) as the absolute value of the normalize force difference $(F_1-F_2)/(F_1+F_2)$ between the sensors increases. Thus, in this embodiment, feedback may be generated which indicates a poor brushing angle (e.g., red LED lit and/or buzzer sound activated) when the absolute value of the force difference $(F_1-F_2)$ exceeds some predetermined threshold value. In an alternate embodiment, a different feedback signal (e.g., green LED lit and/or alternative, positive buzzer sound activated) indicating a good brushing angle may be provided when the absolute value of the force difference $(F_1-F_2)/(F_1+F_2)$ is less than or equal to the predetermined threshold value. It is mentioned that in this case also multiple threshold values can be used, such that e.g. green, orange or red feedback can be given.

Furthermore, in the first, second, third and fourth implementations just described, it may be advantageous for the relevant figure of merit to only be judged at absolute force levels above a certain threshold value of, for example and without limitation, 0.25N. Otherwise, feedback may be given when the brushhead 18 is not really in contact with the teeth.

Moreover, when the brushing action of toothbrush 10 is primarily on the teeth, the readings of first force sensor 30A and second force sensor 30B will, as described herein, provide a good indication of the current brushing angle. However, when the brushing action of toothbrush 10 is on the gum line, readings from first force sensor 30A and second force sensor 30B may nonetheless falsely indicate ideal brushing angles (e.g., $F_1/F_2>0.8$) because the position of toothbrush 10 on the gums may yield a dominant signal from the first force sensor 30A ($F_1$) due to the gum orientation. According to one exemplary, non-limiting particular implementation, this issue may be overcome by employing the concept disclosed herein in combination with the concept described in WO 2014/097242, entitled "Plaque Detection Using A Stream Probe," owned by the assignee of the present invention, the disclosure of which is incorporated herein by reference. In particular, WO 2014/097242 describes a system wherein signals from a stream probe may be used to obtain information indicating that a brushhead is on the gums. Using this information, more optimized feedback of brushhead orientation according to the concept disclosed herein may be provided. In particular, an indication that brushhead 18 is positioned on the gums obtained in the manner described in WO 2014/097242 may be used as a check for situations wherein readings from first force sensor 30A and second force sensor 30B indicate ideal brushing angles, such that if such readings indicate ideal brushing angles yet it is determined that brushhead 18 is on the gums, feedback indicating ideal brushing angles will not be provided.

Thus, toothbrush 10 shown in FIGS. 1 and 2 and the method of operation shown in FIG. 3 provide a system wherein users may be automatically encouraged to employ preferred brushing angles to increase brushing effectiveness and efficiency.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of operating a toothbrush having a brush head, the toothbrush defining a first longitudinal axis, and the brush head having a plurality of bristles extending along a second longitudinal axis, the method comprising the steps of:
operating a toothbrush;
generating first information indicative of a first force exerted by the brush head against a brushing surface at a first angle relative to the first longitudinal axis and the second longitudinal axis and second information indicative of a second force exerted by the brush head against the brushing surface at a second angle relative to the first longitudinal axis and the second longitudinal axis, the second angle being different than the first angle;
wherein each of the plurality of bristles extends in a direction substantially perpendicular to the first longitudinal axis, wherein the first force is in a direction substantially perpendicular to the first longitudinal axis and substantially parallel to the second longitudinal axis and the second force is in a direction substantially perpendicular to second longitudinal axis and is at an angle $\alpha_1$ that is not substantially perpendicular to first longitudinal axis, wherein the first information is $F_1$ and the second information is $F_2$;
determining if a current brushing angle of the brush head relative to the brushing surface during operating of said toothbrush is above or below one or more predetermined threshold values by comparing a ratio of $F_1/(F_1+F_2/\cos\alpha_1)$ to said one or more predetermined threshold values; and
providing user perceptible feedback of the current brushing angle of the toothbrush.

2. A method of operating a toothbrush having a brush head, the toothbrush defining a first longitudinal axis, and the brush head having a plurality of bristles extending along a second longitudinal axis, the method comprising the steps of:
operating a toothbrush;
generating first information indicative of a first force exerted by the brush head against a brushing surface at a first angle relative to the first longitudinal axis and the second longitudinal axis and second information indicative of a second force exerted by the brush head against the brushing surface at a second angle relative to the first longitudinal axis and the second longitudinal axis, the second angle being different than the first angle;

wherein each of the plurality of bristles extends in a direction substantially perpendicular to the first longitudinal axis, wherein the first force is in a direction substantially perpendicular to the first longitudinal axis and substantially parallel to the second longitudinal axis and the second force is in a direction substantially perpendicular to second longitudinal axis and is at an angle $\alpha_2$ that is not substantially perpendicular to first longitudinal axis, wherein the first information is $F_1$ and the second information is $F_2$;

determining if a current brushing angle of the brush head relative to the brushing surface during operating of said toothbrush is above or below one or more predetermined threshold values by comparing a ratio of $F_1/(F_1+F_2/\sin \alpha_2)$ to said one or more predetermined threshold values; and providing user perceptible feedback of the current brushing angle of the toothbrush.

\* \* \* \* \*